United States Patent
Stenzler et al.

(12) 
(10) Patent No.: US 9,108,008 B2
(45) Date of Patent: Aug. 18, 2015

(54) BUBBLE CONTINUOUS POSITIVE AIRWAY PRESSURE DEVICE

(71) Applicant: B & B Medical Technologies, Inc., Carlsbad, CA (US)

(72) Inventors: Alex Stenzler, Long Beach, CA (US); Steve Han, Huntington Beach, CA (US)

(73) Assignee: S & T Medical Technologies, Inc., Carlsbad, CA (US)

(*) Notice: Subject to any disclaimer, the term of this patent is extended or adjusted under 35 U.S.C. 154(b) by 392 days.

(21) Appl. No.: 13/714,913

(22) Filed: Dec. 14, 2012

(65) Prior Publication Data

US 2014/0166013 A1    Jun. 19, 2014

(51) Int. Cl.
*A61M 16/00* (2006.01)
*A61M 16/20* (2006.01)

(52) U.S. Cl.
CPC ............ *A61M 16/0057* (2013.01); *A61M 16/00* (2013.01); *A61M 16/0006* (2014.02); *A61M 16/201* (2014.02); *A61M 2205/3348* (2013.01); *Y10T 29/494* (2015.01)

(58) Field of Classification Search
CPC . A61M 16/00; A61M 16/0006; A61M 16/08; A61M 16/16
USPC ...................................................... 128/204.18
See application file for complete search history.

(56) References Cited

U.S. PATENT DOCUMENTS

| | | | | |
|---|---|---|---|---|
| 4,407,279 A | * | 10/1983 | Tschernezky | 128/200.11 |
| 6,805,120 B1 | * | 10/2004 | Jeffrey et al. | 128/204.23 |
| 6,988,497 B2 | * | 1/2006 | Levine | 128/203.27 |
| 7,077,154 B2 | * | 7/2006 | Jacobs et al. | 137/251.1 |
| 8,225,787 B2 | * | 7/2012 | Newman, Jr. | 128/204.18 |
| 8,235,042 B2 | * | 8/2012 | Newman, Jr. | 128/204.18 |
| 2005/0072470 A1 | * | 4/2005 | Jacobs et al. | 137/251.1 |
| 2009/0194108 A1 | * | 8/2009 | Newman, Jr. | 128/204.18 |
| 2010/0282256 A1 | * | 11/2010 | Loescher et al. | 128/204.18 |
| 2011/0073112 A1 | * | 3/2011 | DiBlasi et al. | 128/205.24 |

FOREIGN PATENT DOCUMENTS

| | | | |
|---|---|---|---|
| EP | 2450073 A1 | * | 5/2012 |
| WO | WO 2014085431 A1 | * | 6/2014 |

OTHER PUBLICATIONS

Lee KS, Dunn MS, et al. A Comparison of Underwater Bubble Continuous Positive Airway Pressure in Premature Neonates Ready for Extubation. Biol. Neonate 73: 69-75. 1998.

Pillow JJ, Travardi JN. Bubble CPAP: is the noise important? An in vitro study. Pediatr. Res 2005; 57: 826-830.

(Continued)

*Primary Examiner* — Lynne Anderson
*Assistant Examiner* — Kathryn E Ditmer
(74) *Attorney, Agent, or Firm* — Richard D. Clarke

(57) ABSTRACT

The present invention is directed to a Continuous Positive Airway Pressure Device as an apparatus configured to provide positive airway pressure in a respiratory circuit that comprises a container configured to be filled to a preselected level with liquids; a drop tube assembly comprising a hollow gas tube rotatably mounted in said container having an upper end extending a static distance outwardly of the container and connected to a respiratory circuit downstream of a user, and a hollow drop tube reciprocally movable upwardly and downwardly in the liquid in response to rotational movement of the gas tube. The container is provided with a gas vent and a liquid fill port.

20 Claims, 8 Drawing Sheets

(56) References Cited

OTHER PUBLICATIONS

Avery ME, Tooley WH, Keller JB, Hurd SS, Bryan MH, Cotton RB, Epstein MF, Fitzhardinge PM, Hansen CB, Hansen TN. Is chronic lung disease in low birth weight infants preventable? A survey of eight centers. Pediatrics 1987;79:26-30.

AM De Klerk, RK De Klerk. Nasal continuous positive airway pressure and outcomes of pre-term infants. J. Paediatr. Child Health 2001; 114: 697-702.

Marter LJ, Pagano M, et al. Do Clinical Marker of Barotrauma and Oxygen Toxicity Explain Interhospital Variation in Rates of Chronic Lung Disease? Pediatrics, vol. 105 No. 6: 1194-1202. Jun. 2000.

\* cited by examiner

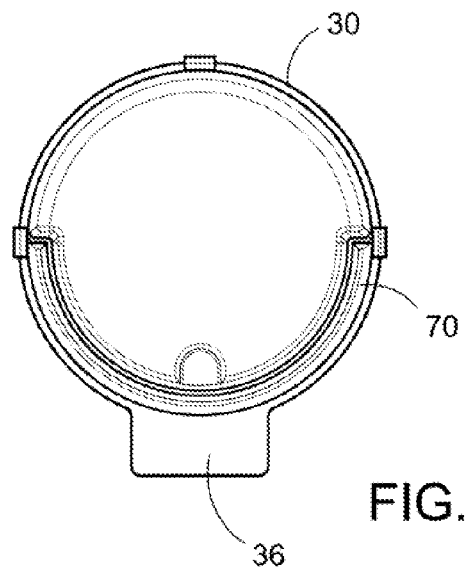
FIG. 11
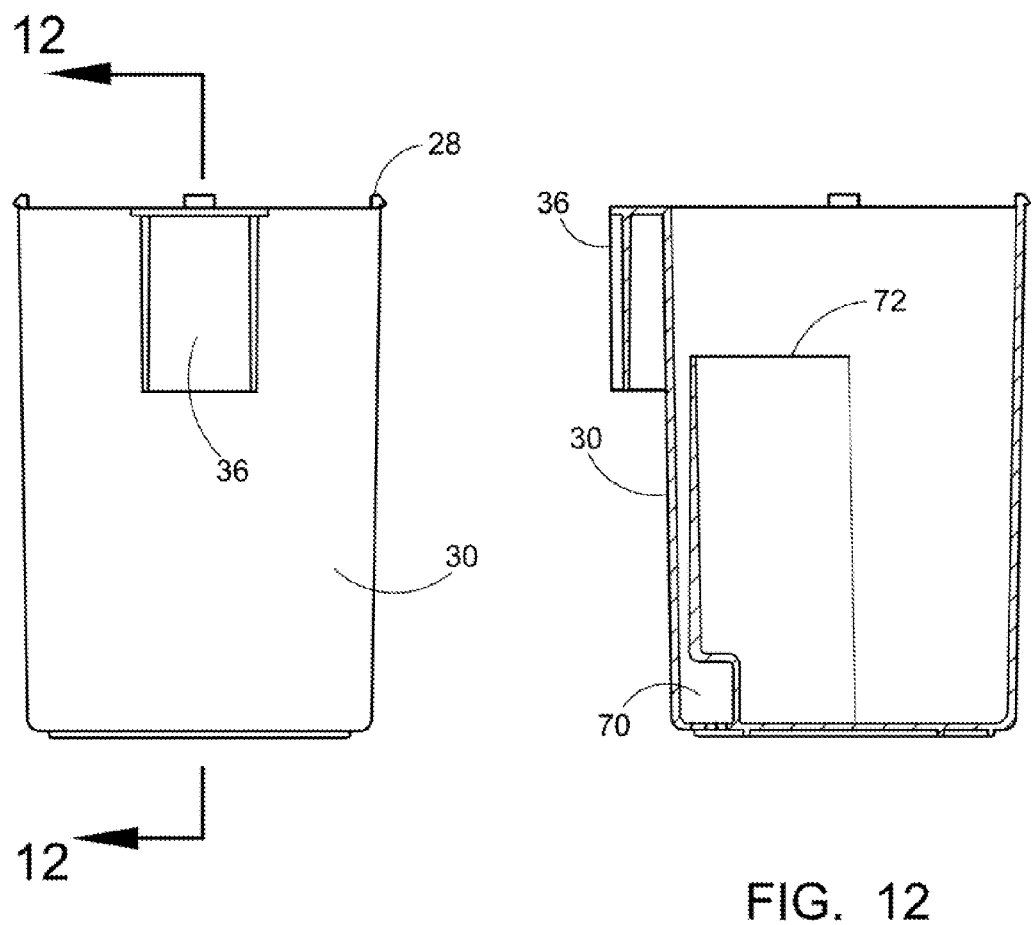
FIG. 10
FIG. 12

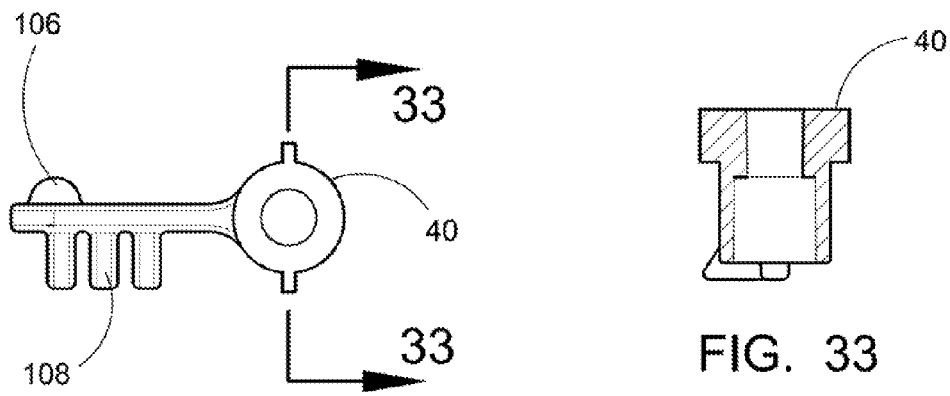
FIG. 32
FIG. 33
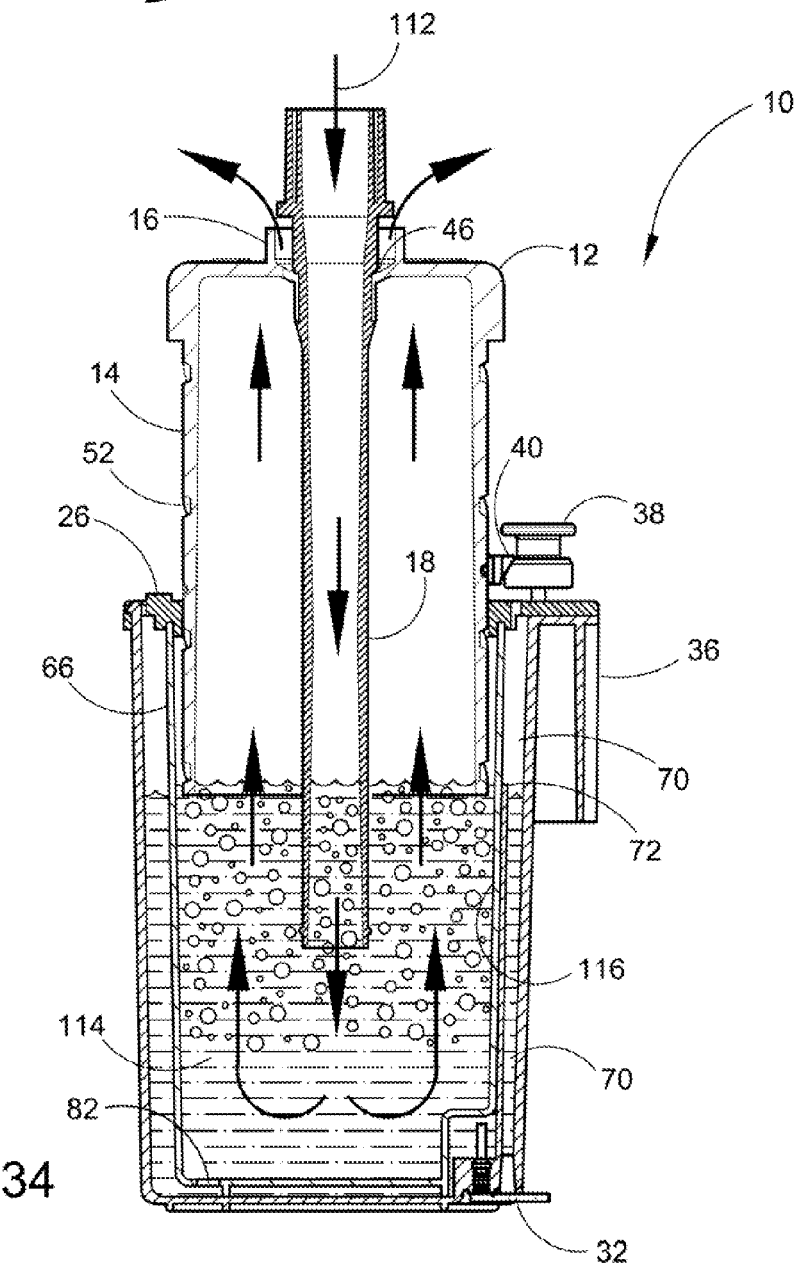
FIG. 34

BUBBLE CONTINUOUS POSITIVE AIRWAY PRESSURE DEVICE

FIELD OF THE INVENTION

This application provides a bubble CPAP (Continuous Positive Airway Pressure device). It works, in combination with a CPAP system, to provide respiratory support to newborn infants who have underdeveloped respiratory systems. The bubble CPAP acts as a pressure generator and water bottle pressure relief device which stabilizes the outgoing infant's air pressure to a desired level by maintaining the exhalation tube under a specific depth of water.

BACKGROUND OF THE INVENTION

Most respiratory diseases of the neonate occur as a result of the immaturity of the premature neonate's lungs. Despite stimulation, the normal process involved in the first breath does not occur. The respiratory system is underdeveloped and adequate gas exchange cannot take place. With this, there is a need for respiratory support.

The bubble CPAP with the combined effects of CPAP and pressure oscillations from the bubbles provides a lung protective, safe and effective method of respiratory support to spontaneously breathing neonates.

The Bubble CPAP effectively maintains Functional Residual Capacity (FRC). Most lung diseases that lead to respiratory failure are commonly associated with a reduced FRC. Maintaining FRC is very important to premature neonates who have a greater tendency of airway closure when FRC falls below closing volume.

The bubble CPAP helps reduce the infant's Work of Breathing (WOB). In a prospective randomized cross over trial performed by Lee, Dunn et. al. (see Lee K S, Dunn M S, et al, A Comparison of Underwater Bubble Continuous Positive Airway Pressure in Premature Neonates Read for Extubation. Biol. Neonate 73: 69-75.1998 comparing bubble CPAP with ventilator-derived CPAP, results showed that there was a decrease in the infant's minute volume and respiratory rate with bubble CPAP. They observed chest vibrations caused by the pressure oscillations from the bubbling. These pressure oscillations, according to the study, are reverberated back into the infant's airway and may have provided an alternate form of gas exchange through the principle of facilitated diffusion. This physiologic effect of bubble CPAP may help improve gas exchange and reduce the infant's work of breathing. Measurements done in vitro by Pillow and Travadi (see Pillow J J. Travadi J N. Bubble CPAP: is the noise important? An in vitro study. Pediatr. Res 2005; 57: 826-830) as well as in vivo measurements on a baby on bubble CPAP confirmed that the pressure oscillations from the bubbling are transmitted into the neonate's airway and lungs.

The bubble CPAP may reduce the need for intubation and mechanical ventilation. In the multi-center comparative study of Avery, et. al. (see Avery M E, Tooley W H, Keller J B, Hurd S S, Bryan M H, Cotton R B, Epstein M E, Fitzhardinge P M, Hansen C B, Hansen N. Is chronic lung disease in low birth weight infants preventable? A survey of eight centers. Pediatrics 1987; 79:26-30) it was noted that the use of bubble CPAP avoided the need for intubation reducing the possibility of airway injury, aspirations and secondary infection associated with the use of the ET tube. Results also showed significant reduction in the need for mechanical ventilation that may minimize the possible incidence of barotrauma.

A historical control study performed by A M De Klerk and R K De Klerk (see A M de Klerk, R K de Klerk. Nasal continuous positive airway pressure and outcomes of preterm infants. J. Paediatr. Child Health 2001; 114: 697-702) in the use of bubble CPAP further confirmed earlier results with data showing marked reduction in intubation and ventilation rates. There was also a decline in the number of days on oxygen and there were trends indicating less number of days on any respiratory support and to an earlier postnatal day of life when respiratory support is no longer needed.

The bubble CPAP tends to reduce the incidence of Chronic Lung Disease (CLD). Early treatment with bubble CPAP for infants with respiratory distress showed a change in the severity and duration of the disease. Significant reduction in the incidence of chronic lung disease which was defined as $O_2$ dependence at 28 days postnatal age or 36 weeks corrected gestation had been noted in some multi-center and comparative studies.

A case-cohort study of Linda Van Marter and colleagues (see Marter L J, Pagano M, et al, Do Clinical Marker of Barotrauma and Oxygen Toxicity Explain Interhospital Variation in Rates of Chronic Lung Disease? Pediatrics, Vol 105 No 6: 1194-1202. June 2000) suggested that barotrauma and oxygen toxicity were linked with CLD and that most of the increased risk of CLD was a result of the initiation of mechanical ventilation. Comparison of different respiratory care in 3 hospitals supported earlier results of reduced incidence of CLD with the use of bubble CPAP. Similar outcomes are being reproduced in hospitals that have used bubble CPAP.

Faster recovery with less lung injury and better respiratory outcomes are possible using a cost-effective respiratory support system such as bubble CPAP.

The Basics of Bubble CPAP systems are really very simple. CPAP systems become confusing when you look at them as multiple hoses, gauges, tubes. To complicate matters more the circuit is connected at one end to a ventilator or blender and at the other end to a baby via a mask or nasal prongs.

Babies in the high humidity environment of an isolate pose unique problems and challenges. Additionally, CPAP therapy does not occur in a vacuum. The bedside nurse and respiratory therapist must understand the system well so that they can deal with the ongoing patient care problems and not spend all their time trying to make the CPAP "work".

In the CPAP circuit, gas flows from the ventilator, blender or flow driver to the humidifier then to the patient. A drainage bag and pressure gauge are present to catch humidifier "rain out" and measure CPAP pressure. All CPAP humidifiers for neonates must be heated between 36.5 and 37.2 degrees Celsius.

The CPAP Interface connects the patient to the CPAP circuit and pressure. Without a good interface the benefits of the CPAP will not be effectively delivered. Nurses and Respiratory Therapists need to be comfortable, fitting and working with the CPAP interface. The three interface types are mask, tube and nasal prongs. Nasal prongs are the best type to use in neonates as the fit is better and the CPAP delivery can easily be assured. Hudson type nasal prongs are well regarded b many CPA P educators as the best type.

The CPAP pressure generator is a simple device that acts to increase the pressure inside the CPAP circuit. The pressure generator must be able to safely keep the pressure at the desired level and safeguard against high system pressures. The pressure generator for Bubble CPAP is a water bottle in which the expiratory limb of the circuit is immersed to a depth in centimeters that equals the desired CPAP pressure. Bubble CPAP may provide what some experts call "high frequency oscillation" effect. In theory this effect could be responsible for improving gas distribution in the lung.

Numerous innovations for the Continuous Positive Airway Pressure Device have been provided in the prior art that are described as follows. Even though these innovations may be suitable for the specific individual purposes to which they address, they differ from the present design as hereinafter contrasted. The following is a summary of those prior art patents most relevant to this application at hand, as well as a description outlining the difference between the features of the Continuous Positive Airway Pressure Device (CPAP) and the prior art.

U.S. Pat. No. 8,235,042 of Lionel Newman Jr. describes an apparatus for providing pressure into which a patient must exhale is provided. The canister has a canister axis and is disposed to hold liquid. The canister also has indicia of pressure on the canister. The apparatus also includes a substantially rigid lid disposed to substantially cover a mouth of the canister and having a first inlet through the lid. The apparatus also includes an adapter in the first inlet. The apparatus also includes a conduit being retained by the adapter such that the conduit is substantially immovable relative to the canister axis.

This patent describes an apparatus for providing pressure into which a patient must exhale but does not have the over loaded water feature that will remove water into the drainable cavity on the inside surface of the outer vessel to provide better adjustment setting of CPAP pressure. It also does not have a selection of different sized end caps for the hollow control tube to control the size of the bubble that is released by the hollow tube to increase or decrease the pressure swings in the respiratory circuit.

U.S. Pat. No. 8,225,787 of Lionel Newman Jr. describes an adjustable airway pressure system is provided. The system may include a cap and a canister. The cap may include a substantially hollow conduit having indicia indicative of a plurality of airway pressure values and adapted to receive and output exhaled gas. The conduit may have screw threads on an exterior surface of the conduit. The cap may also include an adjust collar circumscribing the conduit and having an interior surface with a second plurality of screw threads. The second plurality of screw threads may couple and be complementary to the first plurality of screw threads such that a rotation of the adjust collar causes the conduit to move in a substantially vertical direction. The conduit may be adapted to be adjusted to heights along a continuum. The canister may contain liquid and receive the conduit such that the received exhaled gas is output from the conduit into the liquid.

This patent describes an adjustable airway pressure system but also does not have the over loaded water feature that will remove water into the drainable cavity on the inside surface of the outer vessel to provide better adjustment setting of CPAP pressure. It also does not have a selection of different sized end caps for the hollow control tube to control the size of the bubble that is released by the hollow tube to increase or decrease the pressure swings in the respiratory circuit. It does not have the fine adjustment, having at least 4 adjustment points within 1 cm H20.

Patent No. 2010/0282256 A1 of Thomas C. Loescher et al. describes an apparatus configured to provide positive airway pressure in a respiratory circuit comprises a container configured to be filled to a preselected level with liquids; a drop tube assembly comprising a hollow gas tube rotatably mounted in said container having an upper end extending a static distance outwardly of the container and connected to a respiratory circuit downstream of a user, and a hollow drop tube reciprocally movable upwardly and downwardly in the liquid in response to rotational movement of the gas tube. The container is provided with a gas vent and a liquid fill port.

This patent describes an apparatus configured to provide positive airway pressure in a respiratory circuit system but also does not have the over loaded water feature that will remove water into the drainable cavity on the inside surface of the outer vessel to provide better adjustment setting of CPAP pressure or the inner pressure control vessel. It also does not have a selection of different sized end caps for the hollow control tube to control the size of the bubble that is released by the hollow tube to increase or decrease the pressure swings in the respiratory circuit. It does not have the fine adjustment means, having at least 4 adjustment points within 1 cm H20 using the dimple engagement mechanism engaging in the side of the rotating cap lower cylinder.

U.S. Pat. No. 7,077,154 of Harris C. Jacobs et al. describes an apparatus for effecting bubble CPAP. The apparatus includes a hollow vessel holding a liquid, a cap, and a positionable tube assembly. The positionable tube assembly comprises a guide tube and a positionable tube. The positionable tube is arranged to have a gas introduced through it and is located within the guide tube. The positionable tube is arranged to be slid to various discrete longitudinal positions with respect to the guide tube and to be held in any one of those discrete positions against accidental displacement so that the lower free end of the positionable tube is held at a desired position below the surface of the liquid.

This patent describes an apparatus for effecting bubble CPAP but has a large positionable tube assembly that does not give the precise control required or the different sized end caps for the hollow control tube to control the size of the bubbles. It does not have the fine adjustment means, having at least 4 adjustment points within 1 cm H20 using the dimple engagement mechanism engaging in the side of the rotating cap lower cylinder. It does not have the unique capabilities of the inner pressure control vessel.

U.S. Pat. No. 6,988,497 of Walter Levine describes a humidifier apparatus for operating at an air pressure is disclosed for use with a respiratory therapy breathing apparatus that provides a breathable gas supply to patients requiring higher concentrations of liquid vapor and gas pressure. The humidifier apparatus includes a feed liquid supply bag in fluid communication with a humidifier cartridge via a conduit. The conduit enables air to flow there through to equalize air pressure between the humidifier cartridge and the feed liquid supply bag in response to liquid being supplied to the humidifier cartridge.

This patent describes a humidifier apparatus for operating at an air pressure but does not offer the unique capabilities of the Continuous Positive Airway Pressure Device.

U.S. Pat. No. 6,805,120 of Craig Robert Jeffrey et al. describes a pressure regulator for regulating the expiratory flow in a CPAP system includes submerging a tube into a column of water. Improvements are included for adjusting the level to which the tube is submerged and for ensuring constant water level.

This patent describes a pressure regulator for regulating the expiratory flow in a CPAP system but still does not offer the unique capabilities of the Continuous Positive Airway Pressure Device.

None of these previous efforts, however, provides the benefits attendant with the Continuous Positive Airway Pressure Device. The present design achieves its intended purposes, objects and advantages over the prior art devices through a new, useful and unobvious combination of method steps and component elements, with the use of a minimum number of functioning parts, at a reasonable cost to manufacture, and by employing readily available materials.

In this respect, before explaining at least one embodiment of the Continuous Positive Airway Pressure Device in detail it is to be understood that the design is not limited in its application to the details of construction and to the arrangement of the components set forth in the following description or illustrated in the drawings. The Continuous Positive Airway Pressure Device is capable of other embodiments and of being practiced and carried out in various ways. In addition, it is to be understood that the phraseology and terminology employed herein are for the purpose of description and should not be regarded as limiting. As such, those skilled in the art will appreciate that the conception, upon which this disclosure is based, may readily be utilized as a basis for designing of other structures, methods and systems for carrying out the several purposes of the present design. It is important, therefore, that the claims be regarded as including such equivalent construction insofar as they do not depart from the spirit and scope of the present application.

SUMMARY OF THE INVENTION

The principal advantage of the Continuous Positive Airway Pressure Device is to aide in the care and treatment of respiratory diseases of the neonate that occur as a result of the immaturity of the premature neonate's lungs.

Another advantage of the Continuous Positive Airway Pressure Device is a large dial for easy adjustment.

Another advantage of the Continuous Positive Airway Pressure Device is having two locations for an adjustment number that can be viewed from top and side.

Another advantage of the Continuous Positive Airway Pressure Device is having a self-drainable air vent ports with a wall in the rotating cap around the hollow control tube orifice.

Another advantage of the Continuous Positive Airway Pressure Device is a higher wall to prevent water from coming out of the bottle due to large bubbles.

Another advantage of the Continuous Positive Airway Pressure Device is the smaller hollow control tube compared with other design makes water level more consistent.

Another advantage of the Continuous Positive Airway Pressure Device is the straight hollow control tube lower end outlet creates larger CPAP pressure amplitude (larger pressure swing)

Another advantage of the Continuous Positive Airway Pressure Device is the fine adjustment, having at least 4 adjustment points within 1 cm H20.

Another advantage of the Continuous Positive Airway Pressure Device is the water level stabilizer hole offset from center for water level measurement in the cavity between the outer vessel and inner vessel.

Another advantage of the Continuous Positive Airway Pressure Device is the over loaded water feature that will remove water into the drainable cavity on the inside surface of the outer vessel to provide better adjustment setting of CPAP pressure.

Another advantage of the Continuous Positive Airway Pressure Device is the bottom drain port for overloaded water in the bottle.

Another advantage of the Continuous Positive Airway Pressure Device is the spring loaded button for added safety for making adjustment to CPAP pressure.

Another advantage of the Continuous Positive Airway Pressure Device is the locking feature on the spring loaded button for added safety during use.

Another advantage of the Continuous Positive Airway Pressure Device is the smaller package design for shipping and storing the unit.

The B&B CPAP system is an expiratory pressure system to create a precise and settable pressure within a respiratory circuit.

The Continuous Positive Airway Pressure device has been designed as a vessel within a vessel. The system consists of a double walled vessel and a rotating cap that moves the hollow control tube up and down. The double walled vessel consists of an inner pressure control vessel and an outer water level reading and overflow vessel. A small orifice at the bottom of the inner control vessel is in communication with the outer vessel to allow equalization of water level between the two vessels and to reduce or eliminate the water level fluctuations caused by the bubbling in the inner vessel with the ability to read the water levels in the outer and inner vessels. The system was designed so that the water level remains constant and the hollow control tube is moved up or down to fixed depths to control the pressure.

To fill the system with water, there is a fill port on the top surface of the rotating cap. The fitting is accomplished with a female Luer fitting that will connect with standard medical syringes or water reservoir bags that allow the vessel to be filled. A plug seals the port when it is not in use.

There is a water level line inscribed on the outer surface of the outer vessel to indicate the correct level of water that should be in the vessel. To assure that too much water is not placed in the inner vessel an overflow well in the outer vessel will prevent the water level from rising above the desired height. To keep the overflow well available for accidental overfilling, a drain port connected to the overflow well with a removable plug enables the water in the well to be removed.

To set and maintain the depth of the hollow control tube with a fine and precise setting, the cap lower cylinder has a spiral set of grooves that engage with protrusions on the outer vessel retaining ring. The spiral design allows for small vertical movement in response to large rotational movement. Therefore it is easy for the clinician to control the depth of the hollow control tube. Markers on the top of the rotating cap indicate the depth of the tip of the hollow control tube relative to the depth of the water in the inner vessel.

Parallel to the rotational spiral grooves are a set of spiral dimples in the cylinder of the cap. A mating dimple engaging mechanism is pressed against the dimples by a spring loaded button. To release the latch, the spring loaded button is depressed so that the latch can be moved away from the dimples. When the button is released, a spring under the button lifts the button up and forces the latch back into the dimple at the set height. This prevents accidental movement of the rotating cap that could change the depth of the hollow control tube and therefore the pressure in the respiratory circuit.

Air flows into the top orifice of the hollow control tube that has been designed for securing tubing from a conventional expiratory pressure system. Once the pressure exceeds the depth of the water in cm H20, the air bubbles up through the water and flows out the vents in the rotating cap. Therefore, controlling the depth of the hollow control tube in the water controls the pressure in the respiratory circuit. The wall in the rotating cap around the hollow control tube orifice and the vent ports keeps water from coming out of the bottle due to large bubbles.

To ease mounting for clinical use, a bracket bar is molded into the outer vessel. This bracket bar fits standard respiratory device brackets that mount to poles or rails. Molded into the outer vessel, it assures that the weight of the water is supported by the outer vessel.

To prevent the rotation of the cap from exerting torqueing force on the respiratory circuit tubing, the hollow control tube rotates freely. When the hollow control tube is first inserted into the rotating cap it stays permanently fixed by the means of a barbed attachment to the rotating cap but will still rotate within the orifice in the center of the rotating cap freely.

The small hole in the bottom of the inner vessels allows water to flow from the inner vessel into the outer vessel. The hole is small enough to dampen the oscillation of the water that occurs in the inner vessel from the bubbling of the gas from being transmitted to the outer vessel. This causes the water in the outer vessel to be stable and ease the reading of the water level against the water level marker on the outer vessel.

There is a desire in some situations to increase the amplitude of the pressure swings in the airway by controlling the amplitude of the water oscillations. This is determined by the size of the bubble as gas flows out the hollow tube. To control the size of the bubble that is released by the hollow tube, several optional hollow tip designs can be used to increase or decrease the size of the bubble by accumulating more gas and releasing it as a bolus and therefore increase or decrease the pressure swings in the respiratory circuit.

The foregoing has outlined rather broadly the more pertinent and important features of the present Continuous Positive Airway Pressure Device in order that the detailed description of the application that follows may be better understood so that the present contribution to the art may be more fully appreciated. Additional features of the design will be described hereinafter which form the subject of the claims of this disclosure. It should be appreciated by those skilled in the art that the conception and the disclosed specific embodiment may be readily utilized as a basis for modifying or designing other structures and methods for carrying out the same purposes of the present design. It should also be realized by those skilled in the art that such equivalent constructions and methods do not depart from the spirit and scope of this application as set forth in the appended claims.

BRIEF DESCRIPTION OF THE DRAWINGS

The accompanying drawings, which are incorporated in and form a part of this specification, illustrate embodiments of the Continuous Positive Airway Pressure Device and together with the description, serve to explain the principles of this application.

FIG. 10 depicts a side view of the outer water level reading and overflow vessel.

FIG. 11 depicts a top view of the outer water level reading and overflow vessel.

FIG. 12 depicts a cross section through the outer water level reading and overflow vessel.

FIG. 32 depicts a top view of the dimple engaging mechanism.

FIG. 33 depicts a cross section of the dimple engaging mechanism.

FIG. 34 depicts a cross section operational diagram of the Continuous Positive Airway Pressure Device.

For a fuller understanding of the nature and advantages of the Continuous Positive Airway Pressure Device, reference should be had to the following detailed description taken in conjunction with the accompanying drawings which are incorporated in and form a part of this specification, illustrate embodiments of the design and together with the description, serve to explain the principles of this application.

DETAILED DESCRIPTION OF THE PREFERRED EMBODIMENTS

Figure 1:
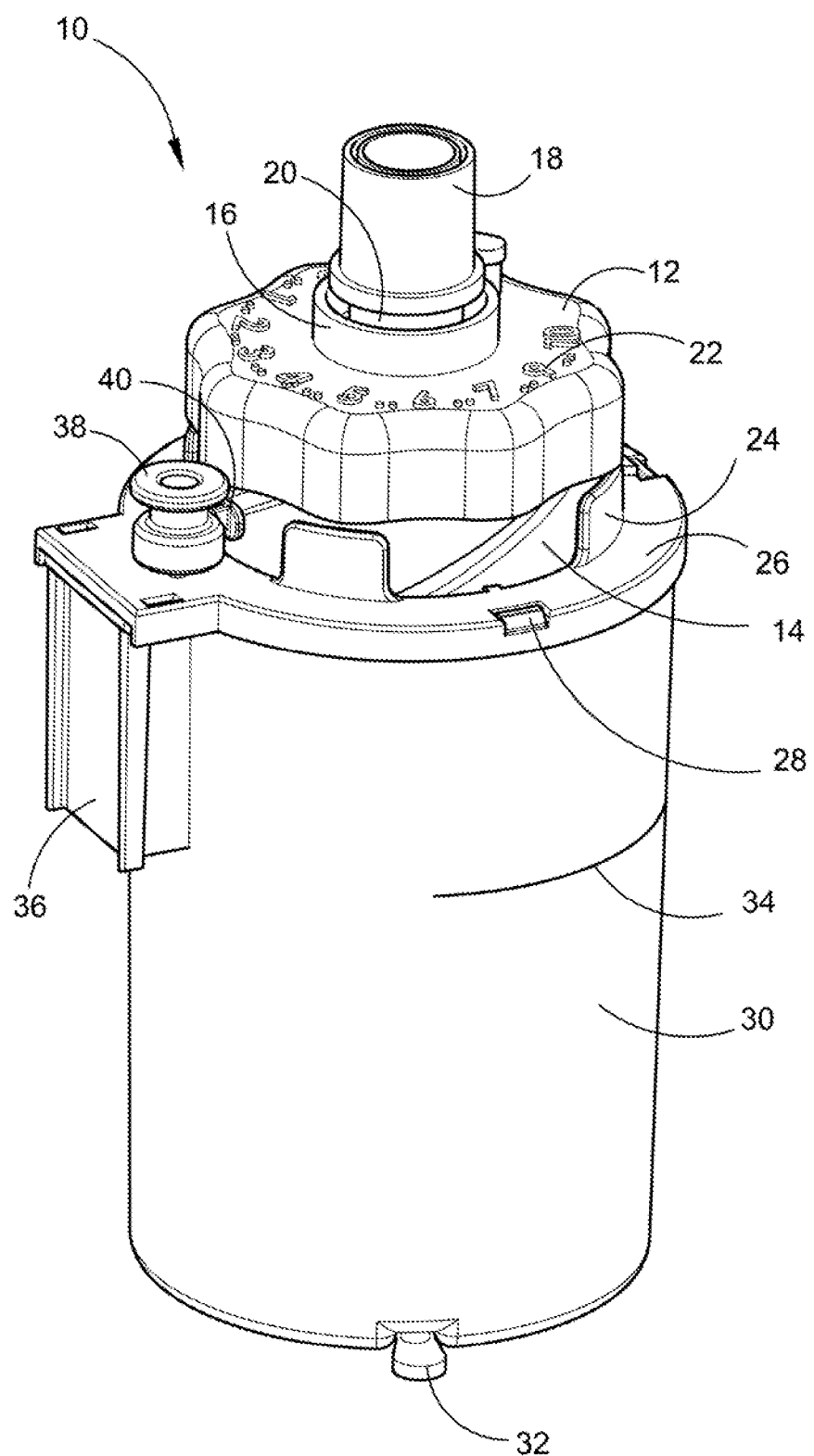
FIG. 1 depicts a Perspective illustration of the assembled Continuous Positive Airway Pressure Device

Referring now to the drawings, wherein similar parts of the Continuous Positive Airway Pressure Device 10 are identified by like reference numerals, there is seen in FIG. 1 a perspective illustration of the assembled Continuous Positive Airway Pressure Device 10 incorporating a rotating cap 12 having the rotating cap lower cylinder 14 permanently attached. The elevated wall 16 on the top of the rotating cap 12 around the hollow control tube 18 orifice 20 keeps water from coming out due to large bubbles. Indicia 22 on the top surface of the rotating cap 12 indicate its relative elevated position. Stop tabs 24 are located around the orifice in the outer vessel retaining ring 26 to maintain the lowest position of the rotating cap 12. The outer vessel retaining ring 26 is fixably attached by the means of barbed connectors 28 on the transparent outer water level reading and overflow vessel 30. The transparent outer water level reading and overflow vessel 30 has an overflow drain plug 32 on the bottom with a water level fill line 34 inscribed on the outer surface and a bracket bar 36 on the side that fits standard respiratory device brackets that mount to poles or rails. A spring loaded locking button 38 on the upper surface of the outer vessel retaining ring 26 couples with the dimple engaging mechanism 40 for precise rotational adjustments.

Figure 2:
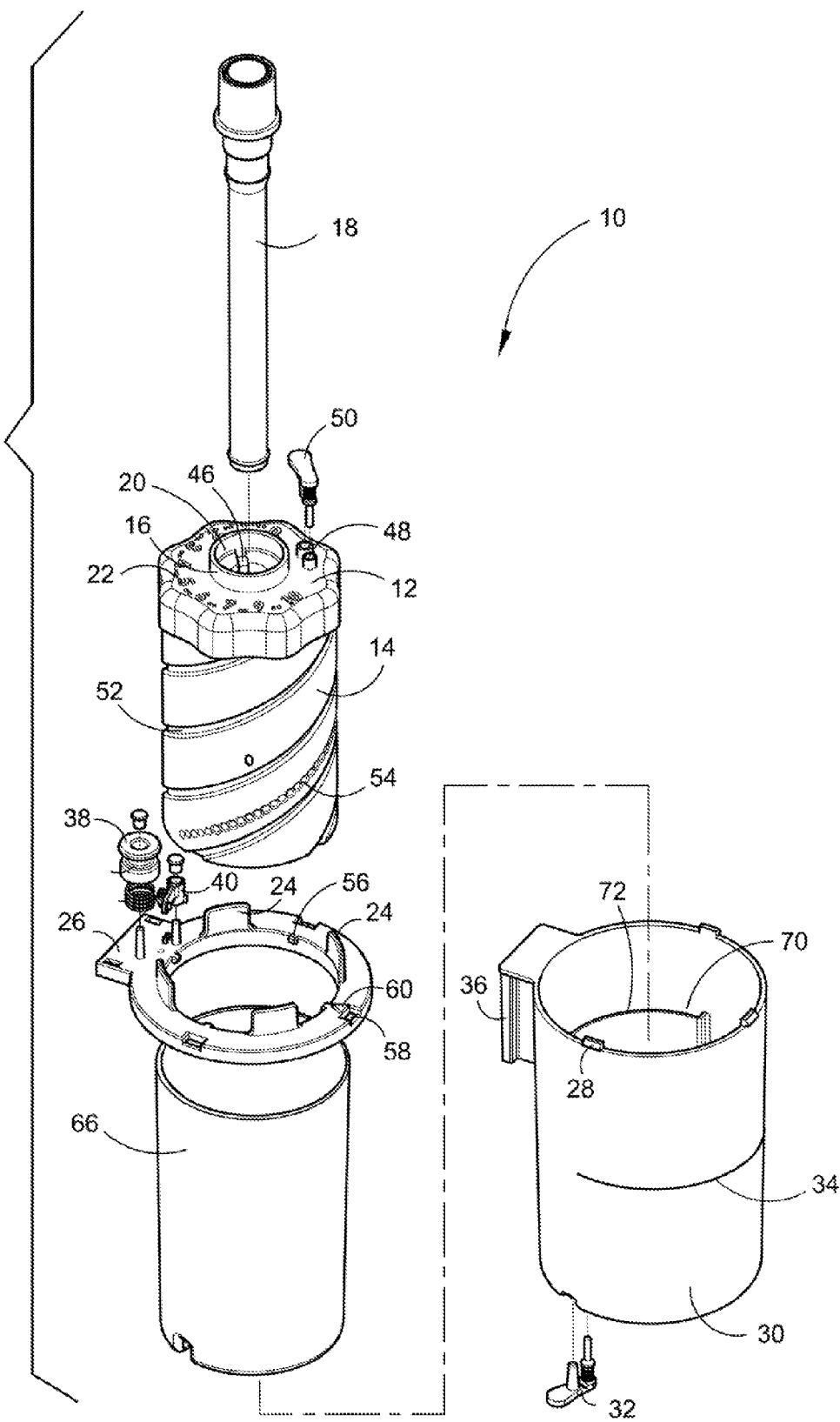
FIG. 2 depicts a perspective view of an exploded Continuous Positive Airway Pressure Device.
Figure 4:
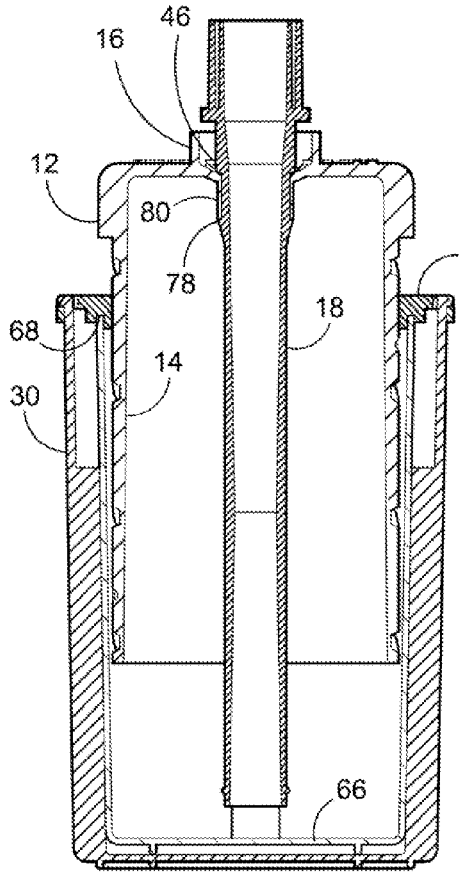
FIG. 4 depicts a cross section through the Continuous Positive Airway Pressure Device.

FIG. 2 depicts a perspective view of an exploded Continuous Positive Airway Pressure Device 10 exposing the hollow control tube 18 and the rotating cap 12 having the rotating cap lower cylinder 14 permanently attached. The elevated wall 16 around the orifice 20 for the hollow control tube 18 exposes one of the vent ports 46 into the central cavity. On the top surface of the rotating cap 12 are the indicia 22 and the fill port 48 with the plug 50. Spiral grooves 52 along with a spiral ring of dimples 54 are on the outer surface of the rotating cap lower cylinder 14. The spiral row of dimples 54 engage with the dimple engaging mechanism 40 when the spring loaded button 38 is pressed. Around the central orifice of the outer vessel retaining ring 26 are four nibs 56 that engage with the spiral grooves 52 when the rotating cap 12 is turned. The spiral row of dimples 54 provide minuscule adjustments while securing the rotating cap 12 with the rotating cap lower cylinder 14 securely in position. Around the periphery of the outer vessel retaining ring 26 are three cavities 58 where the barbed connectors 28 attach on the outer water level reading and overflow vessel 30. An arrow 60 on surface of the outer vessel retaining ring 26 works in conjunction with the indicia 22 on the top surface of the rotating cap 12 indicating its relative elevated position. The inner pressure control vessel 66 seats into a groove 68 (as seen in FIG. 4) on the underside of outer vessel retaining ring 26 shown in FIG. 4. The transparent outer water level reading and overflow vessel 30 has an overflow drain plug 32 on the bottom with a water level fill line 34 inscribed on the outer surface and a bracket bar 36 on the side that fits standard respiratory device brackets that mount to poles or rails. A portion of the overflow well 70 is exposed with its top edge 72 at the same elevation as the water level fill line 34 on the outside of the transparent outer water level reading and overflow vessel 30.

Figure 3:
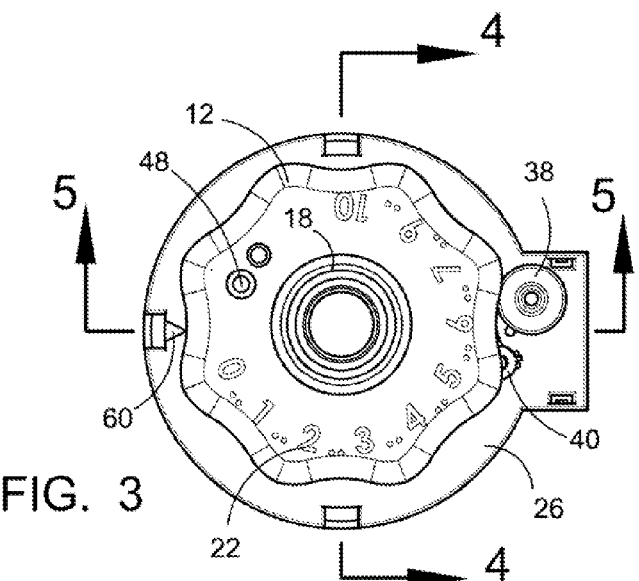
FIG. 3 depicts a top view of the Continuous Positive Airway Pressure Device.

FIG. 3 depicts a top view of the Continuous Positive Airway Pressure Device 10 indicating the locations of the fill port 48 and the indicia 22 on the surface of the rotating cap 12. The arrow 60, the spring loaded button 38 and the dimple engagement mechanism are located on the upper surface of the outer vessel retaining ring 26. The cross section arrows 4-4 and 5-5 indicate the view taken for FIG. 4 and FIG. 5.

FIG. 4 depicts a cross section through the Continuous Positive Airway Pressure Device 10 where the location where the hollow control tube 18 is inserted through the orifice 20 (as seen in FIG. 2) in the outer vessel retaining ring 26. A barbed segment 78 engages with the lower sleeve 80 of the outer vessel retaining ring 26 allowing it to rotate freely but not easily removed.

Figure 5B:
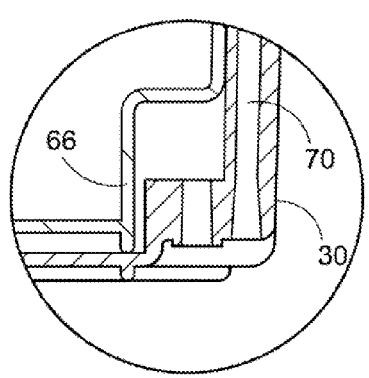
FIG. 5B depicts an enlarged cross section view through the Continuous Positive Airway Pressure Device, illustrating detail in the overflow vessel, overflow well and drain plug location.
Figure 5A:
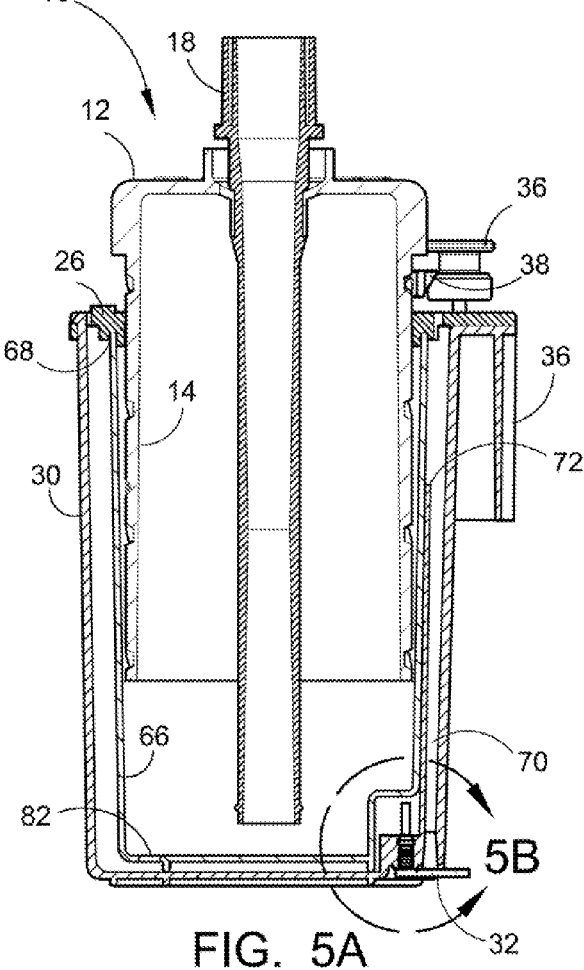
FIG. 5A depicts a cross section through the Continuous Positive Airway Pressure Device.

FIG. 5A depicts a cross section through the Continuous Positive Airway Pressure Device 10 illustrating the location of the overflow well 70 and the overflow drain plug 32. The small hole 82 in the bottom of the inner pressure control vessel 66 allows water to flow to the outer water level reading and overflow vessel 30. The small hole 82 is small enough to dampen the oscillation of the water that occurs in the inner pressure control vessels 66 from the bubbling of the gas from being transmitted to the outer water level reading and overflow vessel 30. This causes the water in the outer vessel to be stabilized and ease the reading of the water level against the water level fill line 34 on the outer vessel 30.

FIG. 5B depicts an enlarged cross section view through the Continuous Positive Airway Pressure Device, illustrating detail in the overflow well and plug location, showing the relationship of the overflow vessel 30, the overflow well 70 and the bottom of the inner pressure control vessel 66. There is no drain in the inner vessel other than the small hole in the bottom portion. The shape in the inner vessel 66 is formed to create space for the outer vessel drain plug 32 (as seen in FIG. 5A). The drain plug 32 only connects with the outer vessel and is directly in line with the pull lines from the tool.

Figure 6:
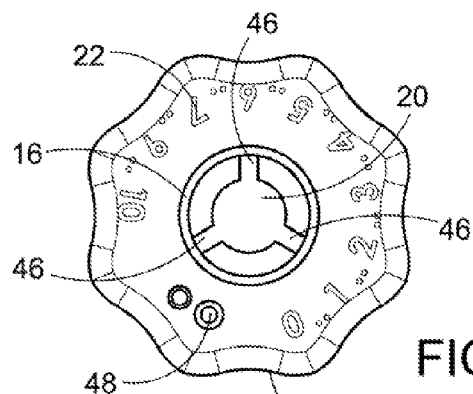
FIG. 6 depicts a top view of the rotating cap having the cap lower cylinder permanently attached.

FIG. 6 depicts a top view of the rotating cap 12 illustrating the locations of the three vent ports 46 in the orifice 20 along with the indicia 22 and the fill port 48.

Figure 7:
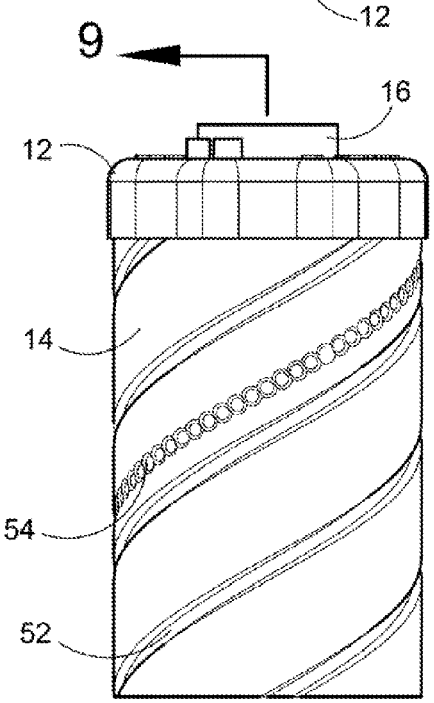
FIG. 7 depicts a side view of the rotating cap having the cap lower cylinder permanently attached.

FIG. 7 depicts a side view of the rotating cap 12 having the rotating cap lower cylinder 14 permanently attached illustrating the set of four spiral grooves 52 and the single spiral row of dimples 54.

Figure 8:
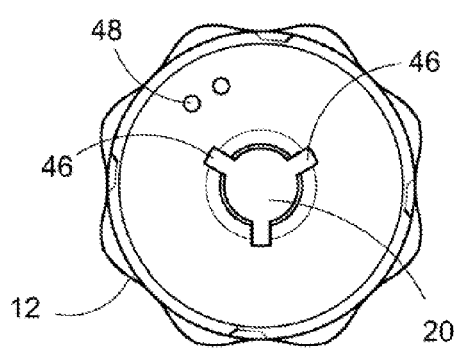
FIG. 8 depicts a bottom view illustrating the inside of the rotating cap.

FIG. 8 depicts a bottom view illustrating the inside of the rotating cap 12 having the cap lower cylinder 14 permanently attached illustrating the three vent ports 46 in the orifice 20 and the location of the fill port 48.

Figure 9:
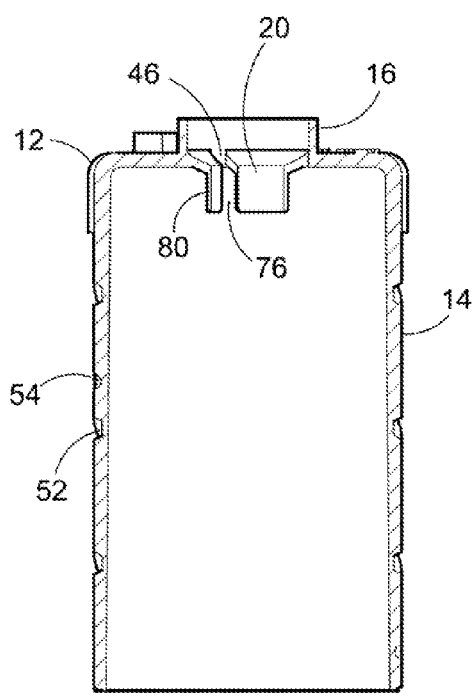
FIG. 9 depicts a cross section through the rotating cap having the cap lower cylinder permanently attached.

FIG. 9 depicts a cross section through the rotating cap 12 having the rotating cap lower cylinder 14 permanently attached illustrating the elevated wall 16 and the orifice 20 with the vent ports 46. The slots 76 in the lower sleeve 80 allow for the flexibility required for expansion when the hollow control tube 18 (as seen in FIGS. 4 and 5, but not shown in FIG. 9) is inserted into secured position but also allow it to rotate freely and still be removed for cleaning.

FIG. 10 depicts a side view of the outer water level reading and overflow vessel 30 illustrating the location of the bracket bar 36 and the barbed connectors 28. Cross section arrows 12-12 indicate the view at which FIG. 12 is taken.

FIG. 11 depicts a top view of the outer water level reading and overflow vessel 30 illustrating the location of the overflow well 70 and the bracket bar 36.

FIG. 12 depicts a cross section through the outer water level reading and overflow vessel 30 illustrating the bracket bar 36 and the overflow well 70 having the top edge 72.

Figure 13:
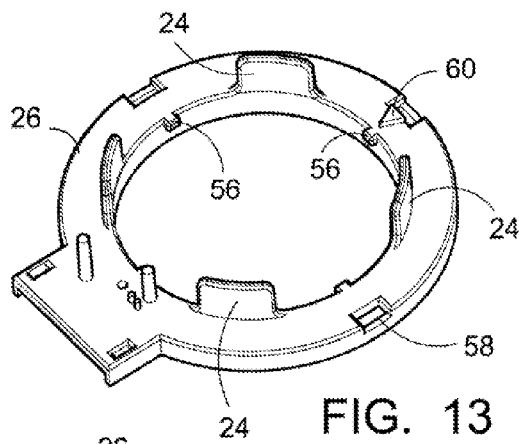
FIG. 13 depicts a perspective view of the top surface of the outer vessel retaining ring.

FIG. 13 depicts a perspective view of the top surface of the outer vessel retaining ring 26 indicating the location of the four stop tabs 24 and the nibs 56 that go into the spiral grooves 52 in the rotating cap lower cylinder 14. The arrow 60 on top surface of the outer vessel retaining ring 26 is shown that works in conjunction with the indicia 22 on the top surface of the rotating cap 12 indicating its relative elevated position.

Figure 14:
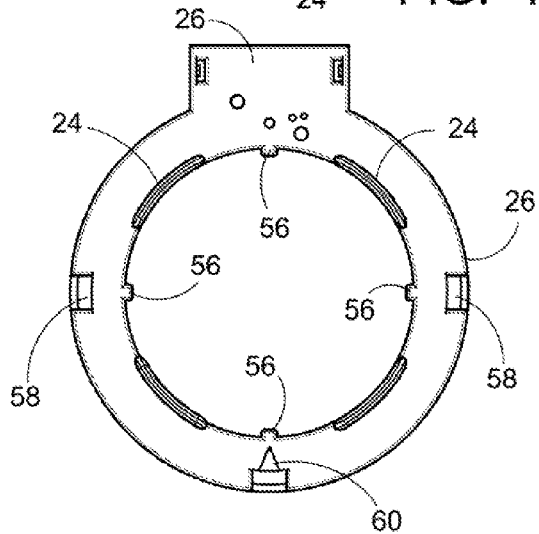
FIG. 14 depicts a top view of the outer vessel retaining ring.

FIG. 14 depicts a top view of the outer vessel retaining ring 26 with the four stop tabs 24 and the nibs 56 along with the cavities 58 where the barbed connectors 28 of the outer water level reading and overflow vessel 30 make contact.

Figure 15:
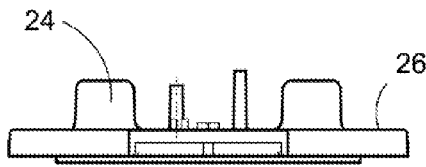
FIG. 15 depicts a side view of the outer vessel retaining ring.

FIG. 15 depicts a side view of the outer vessel retaining ring 26 showing the upright positions of the stop tabs 24 where they will restrain the downward movement of the rotating cap 12 and rotating cap lower cylinder 14.

Figure 16:
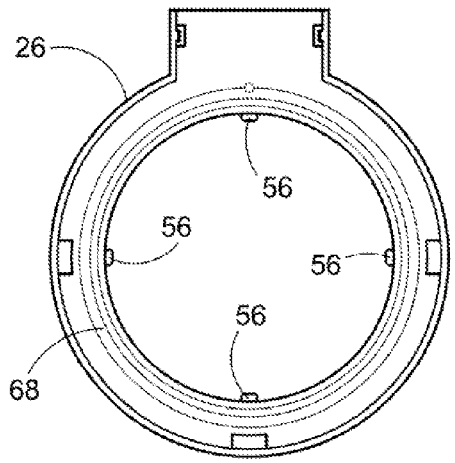
FIG. 16 depicts a bottom view of the outer vessel retaining ring.

FIG. 16 depicts a bottom view of the outer vessel retaining ring 26 illustrating the groove 68 that mates with the top edge of the inner pressure control vessel 66.

Figure 17:
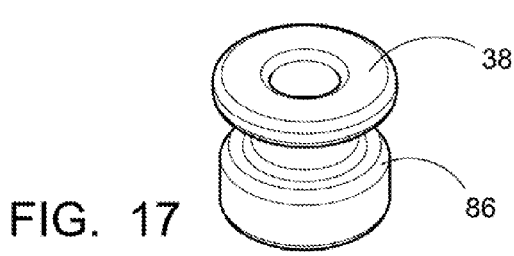
FIG. 17 depicts a perspective view of the spring loaded locking button.

FIG. 17 depicts a perspective view of the spring loaded locking button 38 with the ramped surface 86.

Figure 18:
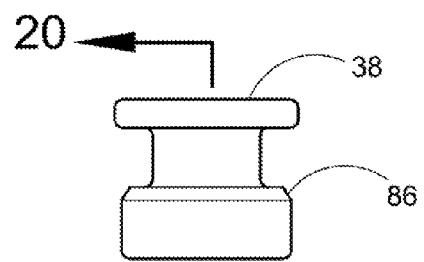
FIG. 18 depicts a side view of the spring loaded locking button.

FIG. 18 depicts a side view of the spring loaded locking button 38 with the ramped surface 86.

Figure 19:
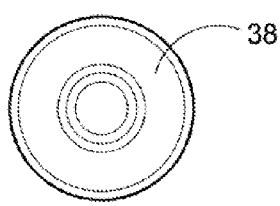
FIG. 19 depicts a top view of the spring loaded locking button.

FIG. 19 depicts a top view of the spring loaded locking button 38.

Figure 20:
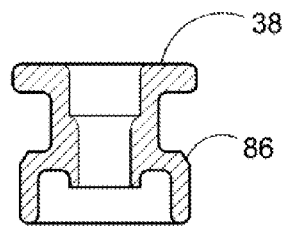
FIG. 20 depicts a cross section through the spring loaded locking button.

FIG. 20 depicts a cross section through the spring loaded locking button 38 with the ramped surface 86.

Figures 21, 22:
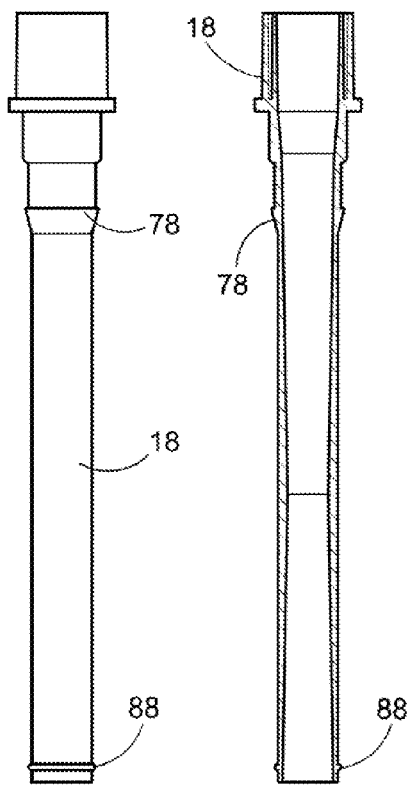
FIG. 21 depicts a side view of the hollow control tube.
FIG. 22 depicts a cross section through the hollow control tube.

FIG. 21 depicts a side view of the hollow control tube 18 with the barbed segment 78 that engages with the lower sleeve 80 of the rotating cap 12. At the lower distal end of the hollow control tube 18 is a ring 88 for securing different end tips 90.

FIG. 22 depicts a cross section through the hollow control tube 18 with the barbed segment 78 that engages with the lower sleeve 80 of the rotating cap 12. At the lower distal end of the hollow control tube 18 is a retaining ring 88 for securing different end tips 90.

Figures 23, 24:
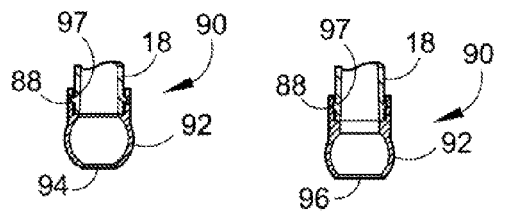
FIG. 23 depicts cross section of an end cap with a bulbous shape having a small sized orifice.
FIG. 24 depicts cross section of an end cap with a bulbous shape having a medium sized orifice.

FIG. 23 depicts cross section of an end tip 90 with a bulbous shape 92 having a small sized orifice 94 with an internal groove 97 that will mate with the retaining ring 88 on the hollow control tube 18.

FIG. 24 depicts cross section of an end tip 90 with a bulbous shape 92 having a medium sized orifice 96 with an internal groove 97 that will mate with the retaining ring 88 on the hollow control tube 18.

Figures 25, 26:
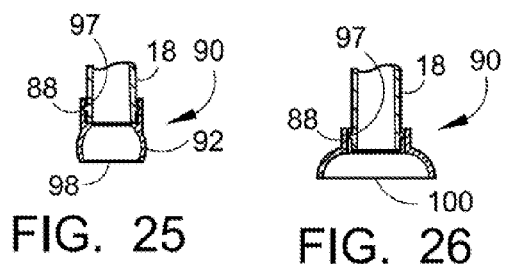
FIG. 25 depicts cross section of an end cap with a bulbous shape having a large sized orifice.
FIG. 26 depicts cross section of an end cap with bell mouth opening.

FIG. 25 depicts cross section of an end tip 90 with a bulbous shape 92 having a large sized orifice 98 with an internal groove 97 that will mate with the retaining ring 88 on the hollow control tube 18.

FIG. 26 depicts cross section of an end tip 90 with bell mouth opening 100 with an internal groove 97 that will mate with the retaining ring 88 on the hollow control tube 18.

Figure 27:
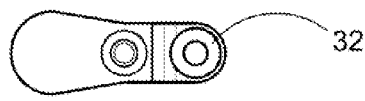
FIG. 27 depicts a top view of the drain plug.

FIG. 27 depicts a top view of the drain plug 32.

Figures 28, 29:
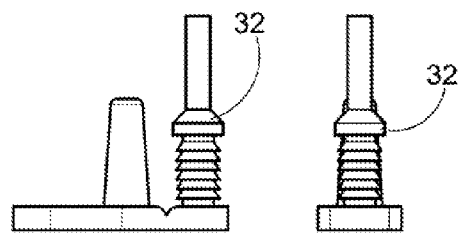
FIG. 28 depicts a side view of the drain plug.
FIG. 29 depicts an end view of the drain plug.

FIG. 28 depicts a side view of the drain plug 32.

FIG. 29 depicts an end view of the drain plug 32.

Figure 30:
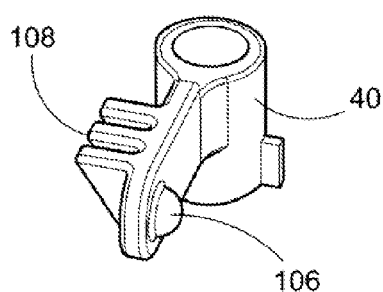
FIG. 30 depicts a perspective view of the dimple engaging mechanism.

FIG. 30 depicts a perspective view of the dimple engaging mechanism 40 with a round protrusion 106 that will mate with any one of the row of dimples 54 on the outer surface of the rotating cap lower cylinder 14. Ramped ribs 108 on the opposite side of the dimple engaging mechanism 40 engage with the ramped surface 86 to lock or release the rotational up and down movement of the rotating cap lower cylinder 14 when the spring loaded locking button 38 is pressed or released.

Figure 31:
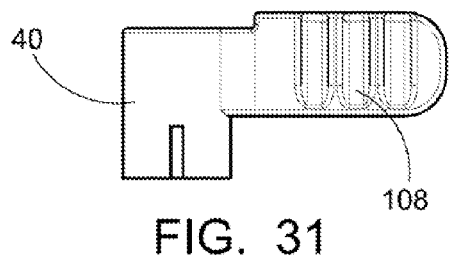
FIG. 31 depicts a side view of the dimple engaging mechanism.

FIG. 31 depicts a side view of the dimple engaging mechanism 40 showing the position of the ramped ribs 108.

FIG. 32 depicts a side view of the dimple engaging mechanism 40 illustrating the locations of the round protrusion 106 and the ramped ribs 108. The cross section arrows 33-33 indicate the view taken for FIG. 33.

FIG. 33 depicts a cross section of the dimple engaging mechanism 40.

FIG. 34 depicts a cross section operational diagram of the Continuous Positive Airway Pressure Device 10 depicting the exhaled air 112 traveling down through the center of the hollow control tube 18 to below the surface of the water 114 to bubble up to the surface and travel out through the vent port 46 in the rotating cap 12. When the turbulence in the water from the bubbles or the water has been over filled, it spills over each end of the top edge 72 of the over flow overflow well 70. The overflow well outer surface 116 is tight against the outer surface of the inner pressure control vessel 66 forcing the water 114 to the outer edges of the overflow well 70. The small hole 82 in the bottom of the inner pressure control vessels 66 allows water to flow to the outer water level reading and overflow vessel 30. The small hole 82 is small enough to dampen the oscillation of the water that occurs in the inner pressure control vessels 66 from the bubbling of the gas from being transmitted to the outer water level reading and overflow vessel 30. This causes the water in the outer vessel to be stabilized and ease the reading of the water level against the water level fill line 34 (not shown in FIG. 34) on the outer vessel.

The Continuous Positive Airway Pressure Device 10 shown in the drawings and described in detail herein disclose arrangements of elements of particular construction and configuration for illustrating preferred embodiments of structure and method of operation of the present application. It is to be understood, however, that elements of different construction and configuration and other arrangements thereof, other than those illustrated and described may be employed for providing a Continuous Positive Airway Pressure Device 10 in accordance with the spirit of this disclosure, and such changes, alternations and modifications as would occur to those skilled in the art are considered to be within the scope of this design as broadly defined in the appended claims.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

We claim:

1. A continuous positive airway pressure device comprising:
    a) a rotating cap having an upper portion including a vent port, a fill port and an integrated lower portion comprising a lower cylinder;
    b) a hollow control tube extending down through said rotating cap lower cylinder portion;
    c) an outer water level reading overflow vessel including a plurality of barbed connectors;
    d) an inner pressure control vessel having an outer vessel retaining ring including a plurality of cavities for mating with said plurality of barbed connectors;
    whereby when assembled and filled with liquid for operation, said outer vessel surrounds said inner vessel and said plurality of barbed connectors securely attach to said plurality of cavities located on said retaining ring and said rotating, cap with said hollow control tube can be vertically adjusted within the liquid held by said inner control vessel.

2. The continuous positive airway pressure device according to claim 1, wherein said rotating cap lower cylinder portion includes spiral grooves and a track of spiraling dimples.

3. The continuous positive airway pressure device according, to claim 1, wherein said retaining ring includes a mating latching dimple engaging mechanism.

4. The continuous positive airway pressure device according to claim 3, wherein said mating latching dimple engaging mechanism includes a vertical spring loaded locking button.

5. The continuous positive airway pressure device according to claim 1, wherein said hollow control tube extending down through said rotating cap lower cylinder portion is vertically retained by said rotating cap and is free to independently rotate when retained.

6. The continuous positive airway pressure device according to claim 1, wherein said rotating cap having an upper portion includes numerical indicia thereon.

7. The continuous positive airway pressure device according to claim 1, wherein said outer water level reading overflow vessel further includes a drain port, removable drain plug and water level fill line.

8. The continuous positive airway pressure device according to claim 1, further including an orifice between said inner pressure control vessel and said outer water level reading overflow vessel such that there is fluid communication there between.

9. The continuos positive airway pressure device according to claim 1, wherein said hollow control tube includes an upper portion having an airway tube connection member and a lower portion having a tip connection member.

10. The continuous positive airway pressure device according to claim 9, further comprising tips having varying tip shapes wherein said hollow control tube lower portion tip connector member is configured to mate with said tips having varying tip shapes, and further wherein said varying tip shapes change the amplitude of the oscillation n the liquid within said inner control vessel.

11. A method for making a continuous positive airway pressure device, comprising the steps of:
providing a rotating cap having a centrally located orifice, an upper portion including a vent port, a fill port and an integrated lower portion comprising a lower cylinder;
providing a hollow control tube;
extending said hollow control tube down through said centrally located orifice in said rotating cap;
providing an outer water level reading overflow vessel including a plurality of barbed connectors;
providing an inner pressure control vessel having an outer vessel retaining ring including a plurality of cavities for mating with said plurality of barbed connectors;
attaching said retaining ring to said inner pressure control vessel and to said rotating cap;
placing said inner pressure control vessel into said outer water level reading vessel;
connecting and securing said inner pressure control vessel to said outer water level reading vessel by snapping together and mating said plurality of cavities with said plurality of barbed connectors;
filling the connected inner pressure control and outer water level reading vessels with liquid;
directing airflow through said hollow control tube and into the liquid in said inner pressure control vessel to create bubbles therein; and
adjusting said hollow control tube vertically within the liquid in said inner pressure control vessel by rotating said rotating cap whereby when vertically adjusted the depth of the hollow control tube within the liquid is changed, thereby altering and the pressure within a respiratory circuit.

12. The method of making a continuous positive airway pressure device according to claim 11, wherein said rotating cap lower cylinder portion includes spiral grooves and a track of spiraling dimples.

13. The method of making a continuous positive airway pressure device according to claim 11, wherein said retaining ring includes a mating latching dimple engaging mechanism.

14. The method of making a continuous positive airway pressure device according to claim 13, wherein said mating latching dimple engaging, mechanism includes a vertical spring loaded locking button.

15. The method of making a continuous positive airway pressure device according to claim 11, wherein said hollow control tube extending down through said rotating cap lower cylinder portion is vertically retained, by said rotating cap and is free to independently rotate when retained.

16. The method of making a continuous positive airway pressure device according to claim wherein said rotating cap having an upper portion includes numerical indicia thereon.

17. The method of making a continuous positive airway pressure device according to claim 11, wherein said outer water level reading overflow vessel further includes a drain port, removable drain plug and water level fill line.

18. The method of making a continuous positive airway pressure device according to claim 11, further including an orifice between said inner pressure control vessel and said outer water level reading overflow vessel such that there is fluid communication there between.

19. The method of making a continuous positive airway pressure device according to claim 11, wherein said hollow control tube includes an upper portion having an airway tube connection member and a lower portion having a tip connection member.

20. The method of making a continuous positive airway pressure device according to claim 19, further comprising tips having varying tip shapes wherein said hollow control tube lower portion tip connector member is configured to mate with said tips having varying tip shapes, and further wherein said varying tip shapes change the amplitude of the oscillation in the liquid within said inner control vessel.

* * * * *